US 6,682,756 B1

(12) United States Patent
Horstmann et al.

(10) Patent No.: US 6,682,756 B1
(45) Date of Patent: Jan. 27, 2004

(54) INDIVIDUALLY DOSED FOIL-FORM PRESENTATION WHICH DECOMPOSES RAPIDLY ON CONTACT WITH LIQUID AND CONTAINS AN ACTIVE SUBSTANCE, IN PARTICULAR AN AROMATIC SUBSTANCE

(75) Inventors: Michael Horstmann, Neuwied (DE); Wolfgang Laux, Diez (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 09/319,909

(22) PCT Filed: Nov. 21, 1997

(86) PCT No.: PCT/EP97/06533

§ 371 (c)(1),
(2), (4) Date: Jul. 15, 1999

(87) PCT Pub. No.: WO98/26764

PCT Pub. Date: Jun. 25, 1998

(30) Foreign Application Priority Data

Dec. 16, 1996 (DE) .......................... 196 52 257

(51) Int. Cl.⁷ .................. A61K 9/70; A61K 9/127; A61K 9/14; A61F 13/00; C12C 7/26
(52) U.S. Cl. ............... 424/443; 424/435; 424/439; 424/450; 424/484; 426/534
(58) Field of Search .............. 426/534; 424/484, 424/439, 450, 443, 435

(56) References Cited

U.S. PATENT DOCUMENTS

| 3,444,858 A | | 5/1969 | Russell |
| 4,128,445 A | * | 12/1978 | Sturzenegger et al. ........ 156/64 |
| 4,946,684 A | | 8/1990 | Blank et al. |
| 5,047,244 A | | 9/1991 | Sanvordeker et al. |
| 5,286,496 A | | 2/1994 | Stapler et al. |
| 5,580,491 A | | 12/1996 | Phillips et al. |
| 6,126,953 A | | 10/2000 | Costa et al. |
| 6,183,757 B1 | | 2/2001 | Beerse et al. |

FOREIGN PATENT DOCUMENTS

| CA | 492 040 | | 4/1953 | |
| EP | 0 219 762 | | 4/1987 | |
| EP | 0 303 445 | A | 2/1989 | |
| EP | 0 303 445 | | 2/1989 | |
| EP | 0 452 446 | | 10/1991 | |
| EP | 0 460 588 | A | 11/1991 | |
| EP | 4600588 | A1 | * 11/1991 | |
| EP | 0 460 588 | | 12/1991 | |
| JP | 54 055 740 | | 5/1979 | |
| JP | 58 192811 | A | 11/1983 | |
| JP | 59 186 912 | | 10/1984 | |
| JP | 06 157 327 | A | 6/1994 | |
| JP | 06 157 327 | | 6/1994 | |
| WO | 95/05416 | | 2/1995 | |
| WO | WO 95/05416 | * | 2/1995 | ............. C08L/1/26 |

* cited by examiner

Primary Examiner—Thurman K. Page
Assistant Examiner—Amy E. Pulliam
(74) Attorney, Agent, or Firm—D. Peter Hochberg; Sean Mellino; Katherine R. Vieyra

(57) ABSTRACT

Individually dosed active substance-containing and, in particular, aromatic-containing, film-shaped administration form, rapidly disintegrating upon contact with a liquid, wherein the aromatic is present as an internal, liposoluble phase in the form of liquid droplets distributed within an outer, solid but water-soluble phase, is characterized in that the said outer phase contains:

Figure 1:
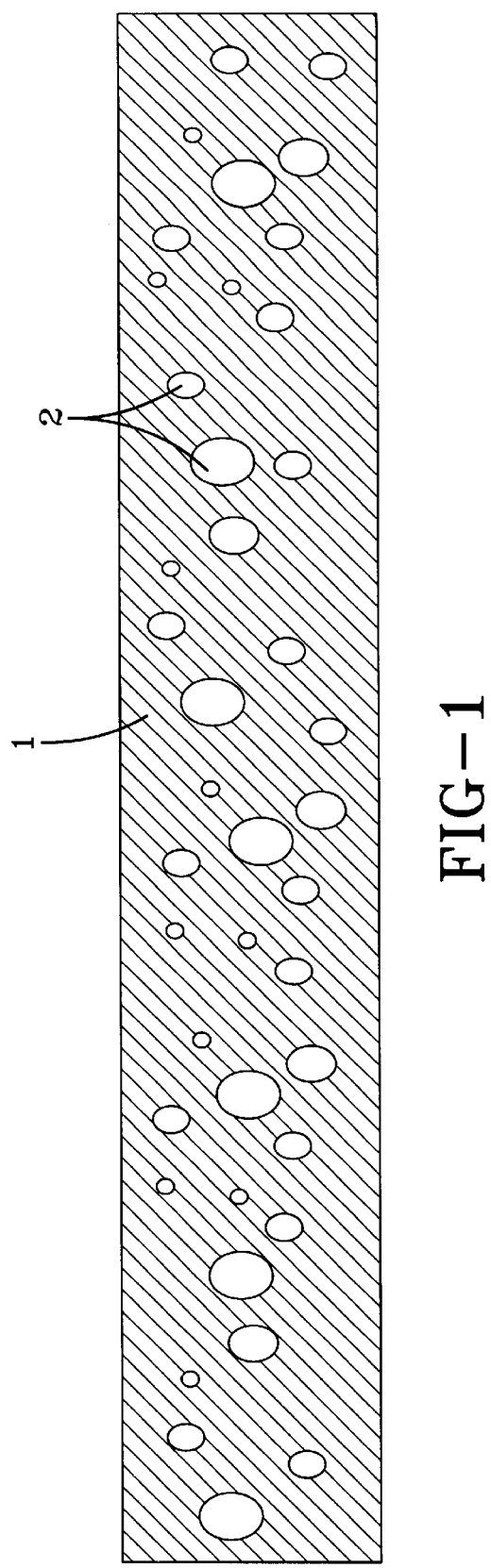

at least 40% (w/w) polyvinyl alcohol 0 to 30% (w/w) of a surface-active substance, and that the constituent amount of the inner phase, relative to the outer phase, is between 0.1 and 30% (w/w), in each case relative to the water-free portions.

10 Claims, 1 Drawing Sheet

INDIVIDUALLY DOSED FOIL-FORM PRESENTATION WHICH DECOMPOSES RAPIDLY ON CONTACT WITH LIQUID AND CONTAINS AN ACTIVE SUBSTANCE, IN PARTICULAR AN AROMATIC SUBSTANCE

The present invention relates to an individually dosed active substance-containing and, in particular, aromatic(s)-containing film-shaped administration form rapidly disintegrating upon contact with a liquid, wherein the aromatic is present distributed as an internal, liposoluble phase, in the form of liquid droplets, in an outer, solid, water-soluble phase.

Flat administration forms to be applied in the oral region and on mucous membranes of the mouth are known. U.S. Pat. No. 3,444,858 describes medicament strips based on a gelatin-like material. Also, pharmaceutical products in the form of a film have already been described in the early 70s, such as, for example, in the New England Journal of Medicine, 289, 533–535 (1973). DE 24 49 865 describes medicinal active substance carriers in the form of a film, containing different active substances and active substance concentrations.

U.S. Pat. No. 4,128,445 discloses technical solutions in loading of carrier material with active substances, and in this context goes into the subsequent addition of active substance preparations by applying them onto pre-fabricated film-shaped preparations. The document describes loading methods in dry and moist form aiming at achieving a uniform, subsequent distribution of active substance on a layer.

The Canadian patent application No. 492 040 describes a process for manufacture of film-shaped preparations employing active substance along with gelatin, agar, gluten, carboxy-vinyl polymer, polyhydric alcohol, vegetable mucilage, wax or water.

Also known are proposals for application of active substance-loaded films or foils outside the pharmaceutical field. Thus, in EP 0 219 762 a water-soluble film of starch, gelatin, glycerol or sorbite is disclosed, which is coated using the roll coating method. In this connection, it is stated that such dosage forms may also be produced employing ingredients of chemical reagents, aromatics and the like.

DE 36 30 603 provides for a flat dosage form, on a carrier material (release film), to be peelable in doses.

Drug-containing film-shaped systems and their advantages are further known from U.S. Pat. No. 5,047,244, these systems comprising a double-layer structure of a water-swellable layer and a nonwater-swellable barrier film. The use of polymers such as polyethylene glycol, the use of colloidal silicon dioxide, of bioadhesive (e.g. carboxy-functional) polymers, but also of polyvinyl alcohol, and of a number of other auxiliary substances is likewise known from the above document.

A preparation suitable for making film-shaped aromatics-containing preparations is described by EP 0 460 588. A composition comprising 20 to 60%-wt. of film-former, 2 to 40%-wt. of gel former, 0.1 to 35%-wt. of active substance or aromatic, and a maximum of 40%-wt. of an inert filling agent is regarded as affording particular advantages. As a gel former, polyvinyl alcohol is mentioned besides other ingredients. However, as it turns out, the gel-forming properties of polyvinyl alcohol are only partially compatible with the film formers mentioned in this document. A portion of 20%-wt., and more, of film former—mostly a sugar derivative, polyethylene glycol, etc.—lead to considerable loss of aroma occurring already in thin-layer drying, which is part of the production process.

Microcapsules are known application forms for protection of volatile or incompatible, finely dispersed products by providing an enclosure with a solid phase (e.g. Bauer/Frömmig, Pharmazeutische Technologie, Stuttgart 1986, 563–566). In the case of microencapsulated aromatics, individual drops of liquid are made processable, e.g. free-flowing, by enclosing. Such forms have already been proposed for application in the oral region, for example according to U.S. Pat. No. 5,286,496. These are, however, fine-grained intermediate products for the manufacture of final products having greater dimensions.

Aromatics-containing sheet-like administration forms for application in the oral region are also known from EP 0 452 446. However, this document does not describe any measures for preventing evaporation of aromatic substance during manufacture and/or storage.

In U.S. Pat. No. 4,946,684 the use of sugar alcohols for increasing moisture stability has been proposed for such forms appearing as flat, solid, open-pored foams, although not for film-shaped forms. However, according to applicant's findings, in the processing of aromatics, the use of high portions of such solubility-increasing additives results in a higher loss of aroma.

Thus, the known methods of producing and assembling film-shaped carriers comprising aromatic ingredient are afflicted with basic disadvantages:

On the one hand, their mechanical strength is dissatisfactory; in particular, the flexural strength and tear resistance of the films obtained is not sufficient for routine applications that are user-friendly.

When adjusted to be softer, the films show the phenomenon of "cold flow", that is they tend to conglutinate with each other. This property is of disadvantage since the user can no longer apply or dose these objects individually. The main disadvantage, however, is to be seen in the fact that aromatics-containing films according to the prior art, by reason of their structure and the selected auxiliary substances, are subject to considerable loss of aroma occurring during manufacture and storage. This loss is a consequence of the overall quantitative loss of aromatics due to migration/diffusion through the base material and subsequent evaporation. At the same time, the quality of the impression of taste is changed, since readily volatile, quality-determining single components are those which are most readily lost.

Based on the above prior art, the present invention has the object of providing an individually dosed administration form of the kind indicated in the introductory generic part of claim 1; which administration form exhibits improved mechanical properties and minimal loss of aroma during production and storage thereof, while avoiding the above-mentioned disadvantages and difficulties.

This object is solved according to the present invention in accordance with the features of claim 1. The active substance-containing internal phase, containing the aromatic substance in the form of liquid droplets, is enclosed in an outer, solid but water-soluble phase containing, in accordance with the characterizing portion of claim 1, portions of polyvinyl alcohol, of surfactants and of filling agents, with the constituent amount of the internal phase being between 0.1 and 30%-wt., relative to the outer phase. Using considerable portions of polyvinyl alcohol, the aromatic is embedded within the film, thereby forming a two-phase system.

The administration form according to the invention disintegrates in the mouth within, at most, 5 minutes, and in the process releases the aromatics contained therein, making them available, preferably, for providing assistance in cosmetic, pharmaceutical and food-technology applications. The products obtained according to the invention are surface-stable, flexible and break-resistant, as well as being largely tear-resistant. The adhesion-reducing rough surfaces exhibit only little static friction and practically no "cold flow".

Regularly, the object of the invention is achieved when the outer phase substantially consists of polyvinyl alcohol, and the constituent amount of the aromatics-containing inner phase relative to the outer phase is between 0.1 and 30% (w/w), preferably between 1 and 5% (w/w), in each case relative to water-free portions. Below a portion of 0.1%-wt. the phases are soluble in each other, above 30%-wt. the outer phase becomes fatty and does no longer result in film-formation.

By adding up to 30% (w/w) of a surfactant to the outer phase, it is possible to improve the homogeneity of the distribution of droplets and of the size thereof, which may be between less than 1 $\mu$m and about 100 $\mu$m. Adding up to 40% (w/w) of a filler does not eliminate the advantages of the invention, but widens the scope of application, for example to the use as dry tooth paste. Suitable for this purpose are silicon dioxide, titanium dioxide, calcium carbonate, calcium sulfate, talcum, calcium phosphate or mixtures of these substances—this enumeration not claiming to be exhaustive. Aroma-enhancing substances such as sodium saccharinate, other sweeteners, salt, and sugar derivatives are just as suitable for improving the taste impression as are low-molecular organic acids, e.g. malic acid, adipic acid, citric acid or glutamic acid.

The film-shaped products obtained, preferably have a thickness between 20 and 300 $\mu$m, their size may advantageously be from 0.5 to 8 $cm^2$.

The polyvinyl alcohol used is preferably a partially hydrolised form, wherein between 1 and 20%, especially preferred: 12%, of the hydroxyl groups have been replaced by acetyl groups.

The core of the invention resides in the state of matter of the aromatic or odorous substance and of further flavouring agents. These substances are essentially etherial oils (volatile, water-insoluble distillates of odoriferous parts of plants) and other volatile odoriferous or flavouring substances having limited miscibility with water. Examples for such substances are phenyl ethanol as component of rose fragrance aromatics, menthol, camphene and pinene in fresh, peppermint-like aromatics, appetite-inducing aromatics, spicing aromatics such as, for example, n-butyl phthalide or cineol, but also aromatics having medicinal applications such as eucalyptus oil and thyme oil. A very broad field is taken up by volatile oils and/or aromatics which are being used as additives in foods, and in prefabricated food additives. Examples for these are the so-called fruit ethers, but also other aromatics such as ethyl vanillin, 6-methylcoumarin, citronellol or n-butyl acetate.

The above-mentioned aromatics, mentioned by way of example, which for the most part are miscible with one another, but not in every ratio with the base substance polyvinyl alcohol, nor with water, are according to the invention encapsulated as small drops embedded within the base substance. This state is characterized in that the aromatic is present in an inner phase, in the form of minute droplets within the solid, but otherwise monolithic, outer phase of the dried polyvinyl alcohol and, optionally, further additives.

Although it is true that the technology of distribution of liquid active substance in the form of droplets within a solid carrier material has been known for a long time, it has hitherto nevertheless been employed only in coacervation, spray-drying and spray-solidification processes, and in processes resulting in powdery products as final products. The present invention, however, describes a distribution state wherein the outer phase is microscopically tangible, thus enabling a simple, monolithic structure of the product.

Advantages with regard to production technology are also obvious: It is prevented that the integrity of drop-shaped initial products which are sensitive to moisture is disturbed during the further processing to a film-like administration form. Also, intermediate steps, increasing energy consumption, are avoided. The simultaneous use of the auxiliary substance polyvinyl alcohol, which is characterized by particularly low diffusibility to etherial oils and to other aromatics, ensures, both in the production as well as in the storage of the finished product, the best possible conservation of the aromatics and flavours contained, as well as protection of said substances against diffusion from the administration form.

Even though the mechanic strength of the system results, in particular, from the use of polyvinyl alcohol, a portion of up to 20% of other water-soluble polymers need not have any detrimental effects on the quality of the product of the invention. Advantageous properties may, with regard to the adjustment of the mechanical product characteristics, also be achieved by addition of polyethylene glycol and other plasticizing additives.

The manufacture and processing of the product according to the invention may be performed in accordance with the methods known to those skilled in the art. Particular reference is made in this context to the prior art known from EP 0 460 588 and DE 36 30 603.

In a preferred method, first, a 30% (w/w) solution of polyvinyl alcohol is dissolved in water. Into this phase is given the pre-weighed amount of aromatic or flavouring substance, while stirring slowly. In this process, a high-shear stirring motion must be avoided. By adjusting the temperature to below 30–40° C. and by adding relatively small amounts of solubillizng additives it is prevented that the sensitive aromatic or flavouring substances become dissolved or are evaporated. Typically, the liquid mass is physically stable for only a few hours, and must be coated immediately, preferably in a layer thickness of about 200–300 $\mu$m, onto a carrier, e.g. a film material or metal roller, and dried. Drying may be effected in a canal dryer at increasing temperatures, not exceeding 80° C., until the desired product hardness is reached. If a lower surface adherence is desired, it is possible to obtain a lustreless surface on the product—by coating onto a dehesively coated material having a rough surface.

As long as pigments and other light-scattering additives do not interfere, the two-phase structure surprisingly enables a translucid to transparent appearance of the film. The light refraction indices of common aromatic substances are typically near the refractive power of polyvinyl alcohol, so that no light scattering results.

Microscopically, however, the disperse state of the aromatic substances can be shown at any time, by colouring of the inner phase with lipophile colourants, e.g. Solvent Red.

EXAMPLE

Preparation of an Administration Form According to the Present Invention 17.0 g polyvinyl alcohol (degree of hydrolysis: 88%) are completely dissolved in 60.0 g water, while stirring, at about 90° C. After cooling, 8.0 g spearmint oil are added thereto and this is slowly stirred for 60 minutes. The resultant, uniformly cloudy, viscous mass is applied in a layer thickness of 400 μm onto 200 μm-strong polyethylene terephthalate film.

The layer is dried for 10 minutes, at room temperature, and is subsequently redried for 8 minutes at 50° C. This results in a clear-transparent film with monolithic appearance, which, upon addition of water, becomes completely dissolved within 60 seconds. After equilibration with 60% relative humidity for 24 hours, the film retains its flexural strength against a bending radius of 1 mm. The surface is dry, has slip, and enables durable storage in stack form.

After 1 week of unpacked storage at 25° C./60% relative humidity, the subjective impression of taste is still unaffected.

The invention will in the following be illustrated by means of a drawing.

The reference numbers designate (seen in cross-section of an administration form according to the invention):

1. Outer, water-soluble phase of the film-shaped administration form.
2. Internal, liposoluble phase, containing aromatics or flavourings.

What is claimed is:

1. Individual film shaped dosage form of liposoluble liquid flavors and fragrances which form rapidly disintegrates upon contact with a water containing liquid, said dosage form consisting essentially of an inner phase of liposoluble liquid droplets of between less the 1 μm and 100 μm distributed within an outer, solid, water-soluble phase, said outer phase containing at least 40% (w/w) polyvinyl alcohol and 0 to 30% (w/w) of a surfactant, and the constituent amount of the said inner phase, relative to the said outer phase, when both phases are water free, is between 0.1 and 30% (w/w), wherein said liposoluble liquid droplets are flavors and fragrances.

2. The administration form of claim 1 wherein the outer phase contains up to 40% (w/w) of a filling agent.

3. The administration form of claim 1 wherein the constituent amount of the inner phase, relative to the outer phase, is between 1 and 5% (w/w), in each case relative to water-free portions.

4. The administration form of claim 1 wherein the filling agent consists of silicon dioxide, titanium dioxide, calcium carbonate, calcium sulfate, talcum, calcium phosphate or mixtures of these substances.

5. The administration form of claim 1 wherein it is present as a film with a thickness of between 20 and 300 micrometers.

6. The administration form of claim 1 wherein it is present as a film having an area between 0.5 and 8 cm$^2$.

7. Individual film shaped dosage form of liposoluble liquid flavors and fragrances which form rapidly disintegrates upon contact with a water containing liquid, said dosage form consisting essentially of an adhesion-reducing, rough surface on at least one side thereof and an inner phase of liposoluble liquid droplets of between less than 1 micrometer and 100 micrometers distributed within an outer, solid, water-soluble phase, said outer phase containing at least 40% (w/w) polyvinyl alcohol and 0 to 30% (w/w) of a surfactant, and the constituent amount of the said inner phase, relative to the said outer phase, when both phases are water free, is between 0.1 and 30% (w/w), wherein said liposoluble liquid droplets are flavors and fragrances.

8. Individual film shaped dosage form of liposoluble liquid flavors and fragrances which form rapidly disintegrates upon contact with a water containing liquid, said dosage form consisting essentially of an inner phase of liposoluble liquid droplets of between less than 1 micrometer and 100 micrometers distributed within an outer, solid, water-soluble phase, said outer phase containing at least 40% (w/w) polyvinyl alcohol and 0 to 30% (w/w) of a surfactant, wherein said polyvinyl alcohol consists essentially of a partially hydrolyzed form wherein up to 20% of the hydroxyl groups are replaced by acetyl groups, and the constituent amount of the said inner phase, relative to the said outer phase, when both phases are water free, is between 0.1 and 30% (w/w), wherein said liposoluble liquid droplets are flavors and fragrances.

9. Individual film shaped dosage form of liposoluble liquid flavors and fragrances which form rapidly disintegrates upon contact with a water containing liquid, said dosage form consisting essentially of up to 20% water soluble polymers and an inner phase of liposoluble liquid droplets of between less than 1 micrometer and 100 micrometers distributed within an outer, solid, water-soluble phase, said outer phase containing at least 40% (w/w) polyvinyl alcohol and 0 to 30% (w/w) of a surfactant, and the constituent amount of the said inner phase, relative to the said outer phase, when both phases are water free, is between 0.1 and 30% (w/w), wherein said liposoluble liquid droplets are flavors and fragrances.

10. Individual film shaped dosage form of liposoluble liquid flavors and fragrances which form rapidly disintegrates upon contact with a water containing liquid, said dosage form consisting essentially of plasticizing additives and an inner phase of liposoluble liquid droplets of between less than 1 micrometer and 100 micrometers distributed within an outer, solid, water-soluble phase, said outer phase containing at least 40% (w/w) polyvinyl alcohol and 0 to 30% (w/w) of a surfactant, and the constituent amount of the said inner phase, relative to the said outer phase, when both phases are water free, is between 0.1 and 30% (w/w), wherein said liposoluble liquid droplets are flavors and fragrances.

* * * * *